US011278064B2

(12) United States Patent
Insley et al.

(10) Patent No.: US 11,278,064 B2
(45) Date of Patent: *Mar. 22, 2022

(54) PERSONAL PROTECTION ARTICLE SYSTEM

(71) Applicant: 3M INNOVATIVE PROPERTIES COMPANY, St. Paul, MN (US)

(72) Inventors: Thomas I. Insley, Lake Elmo, MN (US); Lawrence J. Ptasienski, North Oaks, MN (US); Neal A. Rakow, Woodbury, MN (US); Cristina U. Thomas, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/946,691

(22) Filed: Jul. 1, 2020

(65) Prior Publication Data

US 2020/0375276 A1    Dec. 3, 2020

Related U.S. Application Data

(63) Continuation of application No. 16/433,321, filed on Jun. 6, 2019, now Pat. No. 10,729,186, which is a (Continued)

(51) Int. Cl.
*A41D 13/00* (2006.01)
*G06Q 10/00* (2012.01)
(Continued)

(52) U.S. Cl.
CPC .............. *A41D 13/00* (2013.01); *A61B 42/30* (2016.02); *G06Q 10/0833* (2013.01); *G06Q 10/20* (2013.01); *G08B 21/02* (2013.01)

(58) Field of Classification Search
CPC .... A41D 13/00; A61B 42/30; G06Q 10/0833; G06Q 10/20; G08B 21/02
See application file for complete search history.

(56) References Cited

U.S. PATENT DOCUMENTS

| 917,738 A | 4/1909 | Opsal |
| 2,497,632 A | 2/1950 | Shacht |

(Continued)

FOREIGN PATENT DOCUMENTS

| DE | 3611625 | 10/1987 |
| DE | 3932066 | 11/1990 |

(Continued)

OTHER PUBLICATIONS

Beal Services, Notice of Use—Beal Software, 18 pages (2001).

(Continued)

*Primary Examiner* — Nay Tun
(74) *Attorney, Agent, or Firm* — Steven A. Bern

(57) ABSTRACT

The present disclosure is particularly adapted for determining whether the condition of personal protection equipment PPE articles satisfies at least one criterion. A method and system provide at least one predetermined criterion that governs use of the PPE article in a working environment; a PPE article is configured with a smart tag, and a sensing device is provided that is configured to sense data in a working environment related to the predetermined criterion. Acquired data from the sensing device and the smart tag are processed in a data processing system to determine whether the condition of the PPE article satisfies the at least one predetermined criterion.

20 Claims, 5 Drawing Sheets

Related U.S. Application Data continuation of application No. 15/905,774, filed on Feb. 26, 2018, now Pat. No. 10,349,686, which is a continuation of application No. 12/671,930, filed as application No. PCT/US2008/074205 on Aug. 25, 2008, now Pat. No. 9,901,125.

(60) Provisional application No. 61/124,830, filed on Aug. 31, 2007.

(51) Int. Cl.
*A61B 42/30* (2016.01)
*G06Q 10/08* (2012.01)
*G08B 21/02* (2006.01)

(56) References Cited

U.S. PATENT DOCUMENTS

| | | |
|---|---|---|
| 3,473,199 A | 10/1969 | Gerhard |
| 3,474,559 A | 10/1969 | Hunt |
| 3,636,594 A | 1/1972 | Faivre |
| 3,751,835 A | 8/1973 | Smith |
| 4,139,956 A | 2/1979 | Sharrow |
| 4,242,777 A | 1/1981 | Bourard |
| 4,512,096 A | 4/1985 | Heidecker |
| 4,553,633 A | 11/1985 | Armstrong |
| 4,590,374 A | 5/1986 | Brewster |
| 4,612,719 A | 9/1986 | De Jong |
| 4,656,463 A | 4/1987 | Anders |
| 5,023,597 A | 6/1991 | Salisbury |
| 5,164,707 A | 11/1992 | Rasmussen |
| 5,552,772 A | 5/1996 | James |
| 5,584,133 A | 12/1996 | Motooka |
| 5,666,010 A | 9/1997 | Stratiotis |
| 5,758,443 A | 6/1998 | Pedrazzini |
| 5,796,341 A | 8/1998 | Stratiotis |
| 5,832,761 A | 11/1998 | Chen |
| 5,914,913 A | 6/1999 | Shriqui |
| 5,971,282 A | 10/1999 | Rollender |
| 5,973,559 A | 10/1999 | Nicholson |
| 5,973,602 A | 10/1999 | Cole |
| 6,000,396 A | 12/1999 | Melker |
| 6,040,777 A | 3/2000 | Ammann |
| 6,100,806 A | 8/2000 | Gaukel |
| 6,144,301 A | 11/2000 | Frieden |
| 6,186,140 B1 | 2/2001 | Hoague |
| 6,239,737 B1 | 5/2001 | Black |
| 6,276,179 B1 | 8/2001 | Janssen |
| 6,314,183 B1 | 11/2001 | Causey |
| 6,346,886 B1 | 2/2002 | De La Huerga |
| 6,472,988 B1 | 10/2002 | Feld |
| 6,568,354 B1 | 5/2003 | Wasserman |
| 6,666,170 B1 | 12/2003 | Hilpert |
| 6,693,543 B1 | 2/2004 | Stephenson |
| 6,741,174 B2 | 5/2004 | Rhoades |
| 6,747,562 B2 | 6/2004 | Giraldin |
| 6,810,406 B2 | 10/2004 | Schlabach |
| 6,823,617 B2 | 11/2004 | Schweikert |
| 6,853,303 B2 | 2/2005 | Chen |
| 6,897,374 B2 | 5/2005 | Garber |
| 6,965,866 B2 | 11/2005 | Klein |
| 6,995,665 B2 | 2/2006 | Appelt |
| 6,995,673 B1 | 2/2006 | Osredkar |
| 7,002,526 B1 | 2/2006 | Adams |
| 7,019,652 B2 | 3/2006 | Richardson |
| 7,044,373 B1 | 5/2006 | Garber |
| 7,069,100 B2 | 6/2006 | Monette |
| 7,098,793 B2 | 8/2006 | Chung |
| 7,113,094 B2 | 9/2006 | Garber |
| 7,123,151 B2 | 10/2006 | Garber |
| 7,152,035 B1 | 12/2006 | Suhy |
| 7,158,030 B2 | 1/2007 | Chung |
| 7,191,097 B1 | 3/2007 | Lee |
| 7,194,415 B2 | 3/2007 | Hamada |
| 7,263,379 B1 | 8/2007 | Parkulo |
| 7,398,097 B2 | 7/2008 | Parkulo |
| 7,464,001 B1 | 12/2008 | Adams |
| 7,487,098 B2 | 2/2009 | Takagi |
| 7,592,911 B1 | 9/2009 | Hudgens |
| 7,621,846 B2 | 11/2009 | Ainsworth |
| 7,633,387 B2 | 12/2009 | Carmichael |
| 7,652,571 B2 | 1/2010 | Parkulo |
| 7,654,453 B2 | 2/2010 | Mochizuki |
| 7,764,173 B2 | 7/2010 | Yamagiwa |
| 7,768,409 B2 | 8/2010 | Parias |
| 8,085,144 B2 | 12/2011 | Appelt |
| 8,294,580 B2 | 10/2012 | Witwer |
| 2001/0047283 A1 | 11/2001 | Melick |
| 2001/0056359 A1 | 12/2001 | Abreu |
| 2002/0008623 A1 | 1/2002 | Garber |
| 2002/0022969 A1 | 2/2002 | Berg |
| 2002/0026537 A1 | 2/2002 | Schlabach |
| 2002/0031997 A1 | 3/2002 | Lawler, Jr |
| 2002/0188593 A1 | 12/2002 | Moser |
| 2003/0105407 A1 | 6/2003 | Pearce |
| 2003/0137421 A1 | 7/2003 | Herkenrath |
| 2003/0158796 A1 | 8/2003 | Balent |
| 2003/0226010 A1 | 12/2003 | Arima |
| 2004/0004547 A1 | 1/2004 | Appelt |
| 2004/0046710 A1 | 3/2004 | Adams |
| 2004/0088780 A1 | 5/2004 | Bachar |
| 2004/0100384 A1 | 5/2004 | Chen |
| 2004/0131498 A1 | 7/2004 | Kuutti |
| 2004/0229730 A1 | 11/2004 | Ainsworth |
| 2005/0067816 A1 | 3/2005 | Buckman |
| 2005/0114154 A1 | 5/2005 | Wolkowicz |
| 2005/0131578 A1 | 6/2005 | Weaver |
| 2005/0148828 A1 | 7/2005 | Lindsay |
| 2005/0149387 A1 | 7/2005 | O'Shea |
| 2005/0155887 A1 | 7/2005 | Bazany |
| 2005/0251424 A1 | 11/2005 | Sanders |
| 2005/0258238 A1 | 11/2005 | Chapman |
| 2005/0261938 A1 | 11/2005 | Silverbrook |
| 2005/0268916 A1 | 12/2005 | Mumford |
| 2006/0006999 A1 | 1/2006 | Walczyk |
| 2006/0026017 A1 | 2/2006 | Walker |
| 2006/0048998 A1 | 3/2006 | Wolner |
| 2006/0055552 A1 | 3/2006 | Chung |
| 2006/0060512 A1 | 3/2006 | Astle |
| 2006/0064320 A1 | 3/2006 | Postrel |
| 2006/0087440 A1 | 4/2006 | Klien |
| 2006/0117610 A1 | 6/2006 | Silvestri |
| 2006/0117619 A1 | 6/2006 | Costantini |
| 2006/0119525 A1 | 6/2006 | Cohen |
| 2006/0125623 A1 | 6/2006 | Appelt |
| 2006/0125630 A1 | 6/2006 | Parkulo |
| 2006/0184376 A1 | 8/2006 | Graves |
| 2006/0217995 A1 | 9/2006 | Sagnak |
| 2006/0268482 A1 | 11/2006 | Lin |
| 2006/0270471 A1 | 11/2006 | Matthiessen |
| 2007/0001837 A1 | 1/2007 | Larson |
| 2007/0006494 A1 | 1/2007 | Hayes |
| 2007/0010721 A1 | 1/2007 | Chen |
| 2007/0013519 A1 | 1/2007 | Chung |
| 2007/0021971 A1 | 1/2007 | McKinney |
| 2007/0022576 A1 | 2/2007 | Christanio |
| 2007/0067227 A1 | 3/2007 | Ikeda |
| 2007/0078528 A1 | 4/2007 | Anke |
| 2007/0124155 A1 | 5/2007 | White |
| 2007/0124972 A1 | 6/2007 | Ratcliffe |
| 2007/0199567 A1 | 8/2007 | Kanzer |
| 2008/0018472 A1 | 1/2008 | Dasilva |
| 2008/0021717 A1 | 1/2008 | Kaartinen |
| 2008/0021718 A1 | 1/2008 | Kaartinen |
| 2008/0021905 A1 | 1/2008 | Kaartinen |
| 2008/0021919 A1 | 1/2008 | Kaartinen |
| 2008/0106088 A1 | 5/2008 | Rohlf |
| 2008/0106398 A1 | 5/2008 | Rohlf |
| 2008/0108261 A1 | 5/2008 | Swan |
| 2008/0303668 A1 | 12/2008 | Rohlf |

(56) References Cited

U.S. PATENT DOCUMENTS

| | | |
|---|---|---|
| 2009/0058600 A1 | 3/2009 | Krepel |
| 2009/0283596 A1 | 11/2009 | Grummett |

FOREIGN PATENT DOCUMENTS

| | | |
|---|---|---|
| DE | 19816396 | 11/1999 |
| DE | 19842366 | 3/2000 |
| DE | 10008048 | 9/2001 |
| EP | 0692774 | 1/1996 |
| EP | 0788069 | 8/1997 |
| EP | 1516640 | 3/2005 |
| EP | 1091316 | 3/2006 |
| FR | 2593219 | 7/1987 |
| FR | 2704604 | 11/1994 |
| FR | 2801998 | 6/2001 |
| GB | 2398454 | 8/2004 |
| GB | 2422937 | 8/2006 |
| JP | 06-299799 | 10/1994 |
| JP | 2004-343834 | 12/2004 |
| JP | 2005-078222 | 3/2005 |
| JP | 2006-072719 | 3/2006 |
| KR | 10-2006-0101405 | 9/2006 |
| KR | 10-2006-0123918 | 12/2006 |
| WO | 1996-012523 | 5/1996 |
| WO | 1996-012524 | 5/1996 |
| WO | 1997-016963 | 5/1997 |
| WO | 1998-035243 | 8/1998 |
| WO | 1999-019851 | 4/1999 |
| WO | 2001-006401 | 1/2001 |
| WO | 2001-043827 | 6/2001 |
| WO | 2001-044082 | 6/2001 |
| WO | 2001-080198 | 10/2001 |
| WO | 2002-002191 | 1/2002 |
| WO | 2002-085106 | 1/2002 |
| WO | 2002-009957 | 2/2002 |
| WO | 2002-013150 | 2/2002 |
| WO | 2004-008900 | 1/2004 |
| WO | 2004-032019 | 4/2004 |
| WO | 2004-074964 | 9/2004 |
| WO | 2005-024579 | 3/2005 |
| WO | 2005-045461 | 5/2005 |
| WO | 2005-045743 | 5/2005 |
| WO | 2005-048041 | 5/2005 |
| WO | 2005-071978 | 8/2005 |
| WO | 2005-109303 | 11/2005 |
| WO | 2005-110216 | 11/2005 |
| WO | 2005-119590 | 12/2005 |
| WO | 2006-026365 | 3/2006 |
| WO | 2006-123134 | 11/2006 |
| WO | 2008-091164 | 7/2008 |

OTHER PUBLICATIONS

"Brand New—Imperial College London learns the benefits of Safetrak", 1 page (known of prior to Jun. 2006).
Capital Safety ISafe Intelligent Safety System website literature, http://www.capitalsafety.com/Default.aspx?tabid=220 [retrieved from the internet Aug. 21, 2007].
"DBI Sala—User Instruction Manual—Self Retracting Lifeline", 40 pages (©2007).
Durfee., *White Paper on RFID, MEMS, and Their Application in the Field of Construction*, University of Kentucky, Jan. 11, 2002.
"Electronic ID", Allflex USA, Inc., www.allflexusa.com, 6 pages (known of prior to Jun. 2006).
FrenchCreek Production product literature for *The Tracker* Harness Accessories, Feb. 2007.
"HandiGrimpe—Traceability Tools", BEAL, http://www.beal-intervention.com, 6 pages (known of prior to Jun. 2006).
"Harness Accessories" datasheet [online]. FrenchCreek Production, Franklin, PA, Feb. 2007, Retrieved from the Internet: www.frenchcreekproduction.com; 2 pages.
Harnesses, Safetrak, www.safetrack.com, 4 pages (2005).
HDX High Performance Ultra EID Tag—ISO Compliant, Allflex®, http://www.allflexusa.com, 2 pages (2006).
HOA Inspector™, ReefPoint Technology, http://www.reefpt.com, 4 pages (known of prior to Jun. 2006).
INFOCHIP Systems Inc., http://www.infochip.com, web page and 4 on-line brochures, 13 pages (2003).
Initiative Business Systems Respirator Management website literature, http://www.initbusy.com/rpecasestudy.html [retrieved from the internet May 17, 2007].
"ITW Fastex—2-Piece Assembly Ratchet Rivets", ITW Fastex, www.itwfastex.com, 2 pages (known of prior to Jun. 2006).
Kitamura, Using Ubiquitous Networks to Create New Services Based on the Commercial and Public Infrastructure. Sep. 1, 2002, Nomura Research Institute Paper, No. 54 (15 pages).
Low Frequency RFID Evaluation Kit—Refernce Guide, Texas Instruments, 4 pages (Sep. 2002).
"PDAge—Pocket Jobsite® Inspector", http://www.pdage.com, 1 page (2002).
"Pervidi™", http://www.pervidi.com, 11 pages (2005).
Scafftag Safety Systems website: http://scafftag.com, SCAFFTAGSAFETRAK Safety Management Systems—UNITAG®, 5 pages (2005).
Scafftag Safety Systems website: http://scafftag.com, "SCAFFTAGSAFETRAK Safety Management Systems—SAFETRAK", 7 pages (2005).
Scafftag® Press Release: "Micro tag® Makes Harnesses Safer", 1 page (Jun. 2002).
Scafftag® Press Release: "Scafftag® Limited—The Past, Present and Future", 1 page (Jun. 2002).
"Sealed Self Retracting Lifeline—50 ft. cable 3403400", Capital Safety, http://www.capitalsafety.com, 1 page (©2007).
Swedberg, "Safety Harnesses Get Smart", RFID Journal, Jun. 15, 2006.
"Tags", Safetrak, www.safetrack.com, 3 pages (known of prior to Jun. 2006).
"The Tracker", French Creek Production, http://www.frenchcreekproduction.com/tracker.htm, 2 pages (2002).
Tool Hound website: http://www.toolhound.com, 1 page (known of prior to Jun. 2006).
ToolWatch website: http://www.toolwatch.com/accessories labelstags/htm, 2 pages, (© ToolWatch Corporation) (Printed May 24, 2007).
Ward, "RFID: Frequency, Standards, Adoption and Innovation", JISC Technology and Standards Watch, May 2006, pp. 16-20.
WhereNet product literature for *Process Control and Machine Messaging* (2003).
Zgraggen, "Tool Loss: Seeing Red???", Construction Business Owner, pp. 10-12 and 14 (Mar. 2006).
U.S. Appl. No. 11/759,366; IDS submitted Dec. 12, 2007 (2 pages).
U.S. Appl. No. 11/759,158; IDS submitted Oct. 17, 2008 (2 pages).
U.S. Appl. No. 11/759,285; IDS submitted Dec. 6, 2007 (2 pages).

PERSONAL PROTECTION ARTICLE SYSTEM

CROSS REFERENCE TO RELATED APPLICATIONS

This application is a continuation of U.S. application Ser. No. 16/433,321, filed Jun. 6, 2019, now allowed, which is a continuation of U.S. application Ser. No. 15/905,774, filed Feb. 26, 2018, now granted as U.S. Pat. No. 10,349,686, which is a continuation of Ser. No. 12/671,930, filed Feb. 3, 2010, now granted as U.S. Pat. No. 9,901,125, which is a national stage filing under 35 U.S.C. 371 of PCT/US2008/074205, filed Aug. 25, 2008, which claims the benefit of Provisional Application No. 61/124,830, filed Aug. 31, 2007, the disclosure of which is incorporated by reference in their entirety herein.

BACKGROUND

Generally, this disclosure relates to determining a condition of personal protection (PP) articles. More particularly, it relates to methods and systems for determining a condition of a personal protection equipment (PPE) article, wherein the method and system determine whether the condition of the PPE article satisfies at least one criterion.

Maintaining the safety and health of workers is a major concern across many industries. Various rules and regulations have been developed to aid in addressing this concern, which provide sets of requirements to ensure proper administration of personnel health and safety procedures. To help in maintaining worker safety and health, some individuals may be required to don, wear, carry, or otherwise use a PPE article, if the individuals enter or remain in work environments that have hazardous or potentially hazardous conditions. Known types of PPE articles include, without limitation, respiratory protection equipment (RPE), e.g., for normal condition use or emergency response, protective eyewear, such as visors, goggles, filters or shields, protective headwear, such as hard hats, hoods or helmets, hearing protection, protective shoes, protective gloves, other protective clothing, such as coveralls and aprons, protective articles, such as sensors, safety tools, detectors, global positioning devices, mining cap lamps and any other suitable gear.

For example, personnel in the nuclear industry may be required to wear radiation protective clothing and personal dosimeter devices. Law enforcement personnel are sometimes required to wear protective vests and helmets. There are numerous situations in the medical field in which healthcare workers must wear protective gowns, masks, face shields, gloves, etc. Workers in the food service industry are often required to wear hair netting, gloves, masks, etc. For example, there are also many industrial manufacturing scenarios in which personnel are required to wear protective or other specially designed articles in order to ensure a "clean" environment. For example, personnel in the micro-electronics manufacturing industry, biotech industry, laboratory/testing industry, are required to wear PPE articles not only to ensure their own safety, but to protect the equipment and devices which they assemble or perform various procedures with. There are also many industrial manufacturing scenarios in which personnel working in mines, oil refineries, metal grinding facilities, smelting facilities, industrial painting operations or pharmaceutical factories may be required to wear respiratory protection equipment (RPE).

There are many different kinds of RPE's utilized to prevent or reduce inhalations of contaminants, such as hazardous or toxic materials. The RPE's remove specific air contaminants by passing air through their air-purifying element. Proper use of such RPE's is contingent upon their condition and use being in accordance with appropriate sets of rules, guidelines, regulations, certifications, or the like that govern use in a working environment. The rules, guidelines, regulations, certifications may be numerous and may be promulgated from many sources, including business and/or governmental sources. Many traditional RPE's typically do not, for example, include: any mechanism indicating when their ability to remove air contaminants has been reduced, if the workplace in which they are to be used contains contaminants they cannot handle; or if actual use of an RPE is outside recommended or required exposure times in a workplace. As such, determining if RPE'S are properly functioning and/or if their performances are in accordance with recommended or required rules can be quite demanding and at times quite onerous.

Moreover, facilities in which workers use PPE articles are often required to keep detailed records regarding the articles and the processing of them. For example, records may be kept regarding their use, conditions in which they were used, individuals who used them. In addition, records are kept as to when and whether PPE articles are to be serviced, changed-out, subject to maintenance, decontaminated or otherwise processed. As such, significant efforts and extensive recordkeeping must be undertaken. Clearly, making and keeping extensive records that contain all of the above-referenced information present a substantial administrative task. With more than 500,000 air contaminants that may be present in certain work environments, there are numerous rules and regulations to follow and gather information about. Accordingly, companies using such PPE articles have the responsibility to record their compliance with the appropriate rules and regulations. If not, potentially serious and/or costly consequences may rise.

Moreover, despite the extensive records that are required to be collected, adherence to various predetermined criteria is typically the responsibility of the user. Thus, compliance with a particular criterion regarding the condition of a PPE article may become an issue in work environments involving relatively large numbers of workers and/or respirators because of the relative difficulty in tracking worker habits and diligence, in part, due to the wearer not having means of assessing the level of hazards in his/her environment. Clearly, when predetermined criteria are not adhered to, workers are at a higher risk of exposure upon breakthrough of hazardous materials.

Furthermore, the predetermined criteria regarding proper and safe use of PPE articles are often predicated upon assumed work environment conditions prevailing during actual use, such as the kinds and concentrations of particulate in the workplace. Such assumptions also apply to other factors, such as the absence of other contaminants that might adversely affect proper RPE use. Also, such sets of criteria are predicated upon assumptions that the RPE articles will perform as intended. However, potentially serious and/or costly consequences may rise if the noted assumptions change which lead to violations of such rules and regulations. Moreover, it would be of substantial value to determine at which location(s) the assumptions have changed, thereby allowing corrections to be made to the environment or the articles.

Thus, needs exist for electronic methods and systems that overcome or eliminate the drawbacks and shortcomings of known approaches for determining the conditions of PPE articles against at least one criterion governing their use. Accordingly, there is need for electronic methods and systems that enable the conditions of PPE articles, such as RPE articles, to be determined against at least one criterion that governs their use, let alone in a manner that is highly reliable, efficient, and economical.

SUMMARY

In one exemplary embodiment, the present disclosure provides a method for determining a condition of at least one protection equipment PPE article against at least one criterion. Included in the method are: providing at least one PPE article configured with a smart tag; providing at least one predetermined criterion that governs use of the at least one PPE article in a working environment; providing at least one sensing device configured to sense data that is related to the at least one predetermined criterion; acquiring sensed data from the at least one sensing device; retrieving smart tag data from the smart tag; and, processing the sensed data and the smart tag data to determine whether the condition of the at least one PPE article satisfies the predetermined criterion.

In another exemplary embodiment, the present disclosure is directed to a system that comprises: at least one personal protection equipment article configured with a smart tag; at least one predetermined criterion that governs use of at least one personal protection equipment article in a working environment; at least one sensing device configured to sense data that is related to the at least one predetermined criterion; one or more data acquiring devices to acquire sensed data from at least one sensing device and smart tag data from the smart tag; and, a data processor for processing the acquired sensed data and the smart tag data to determine whether the condition of the at least one PPE article satisfies the predetermined criterion.

DETAILED DESCRIPTION

The present disclosure substantially reduces drawbacks and shortcomings of known approaches for determining the conditions of personal protection equipment PPE articles. The foregoing is achieved through a method and system for determining a condition of at least one PPE article against at least one criterion. The method and system provide at least one predetermined criterion that governs use of the PPE article in a working environment. The method and system also provide that the PPE article is configured with a smart tag, and a sensing device that is configured to sense data in a working environment related to the predetermined criterion is also provided. Acquired data from the sensing device and the smart tag are processed to determine whether the condition of the PPE article satisfies the predetermined criterion.

Figure 1:
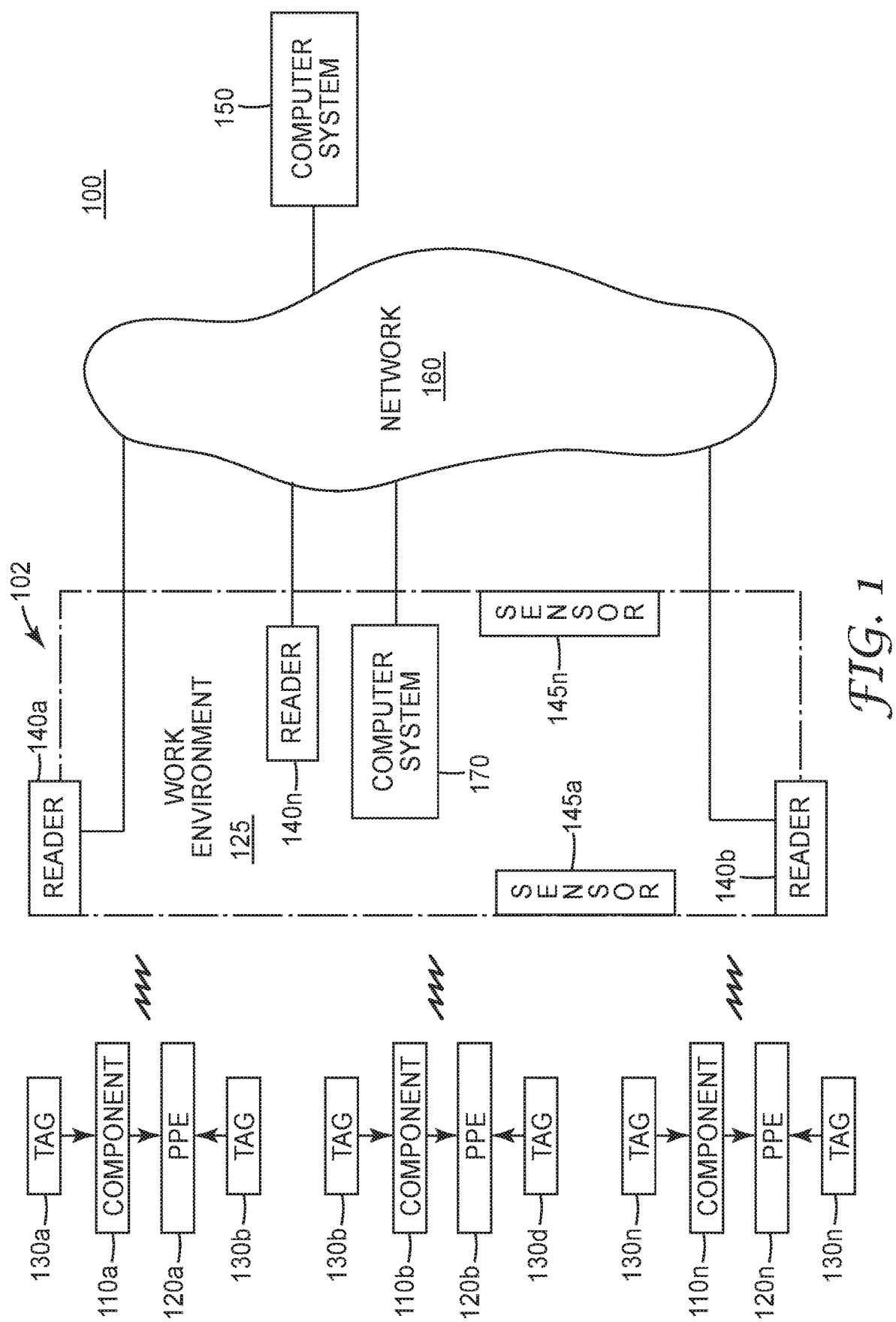
FIG. 1 is a block diagram of an exemplary PPE article condition determining system capable of implementing the process of the present disclosure.

FIG. 1 illustrates a block diagram of a personal protection equipment (PPE) article condition determining system 100, according to one exemplary embodiment of the present disclosure. The PPE article condition determining system 100 includes an information retrieval system 102 networked to a computer system 150. The PPE article condition determining system 100 is utilized for implementing a process for determining a condition of one or more articles of personal protection equipment (PPE) 120a-n (collectively, 120). The personal protection equipment articles may be coupled to a component 110a-n (collectively, 110) for use in combination with the personal protection equipment articles. The PPE articles 120 are to be used in one or more working environments 125 (only one is illustrated). Exemplary working environments include, without limitation, paint shops, petrochemical refineries, mines, smelting facilities, pharmaceutical factories, or the like. "Predetermined criterion or criteria" as the terms are utilized in the present application refers to a set of rules, guidelines, regulations, recommendations, certifications, or the like that governs use of the at least one PPE article in a working environment.

The rules, guidelines, regulations, recommendations, certifications, and the like may be promulgated from any source, including business and/or governmental sources. Examples of the foregoing include, without limitation, the OSHA respirator regulation that requires respirators be National Institute for Occupational Safety and Health (NIOSH) approved, and must be used in compliance with the conditions of (NIOSH) certification. If other than approved types of respirators are used, that would be in violation of appropriate rules and regulations.

For example, government regulations, such as from OSHA, provide for nine classes of filters (i.e., three levels of filter efficiency each with three categories of resistance to filter efficiency degradation). Filter efficiency is the stated percentage of particles removed from the air. Filter efficiency degradation is defined as a lowering of filter efficiency degradation or a reduction in the ability of the filter to remove particles as a result of workplace exposure. Three levels of filter efficiency are 95%, 99%, and 99.97%. The three categories of resistance to filter efficiency degradation are labeled N, R, and P. The class of filter will be clearly marked on the filter, filter package, or respirator box. For example, a filter marked N95 would mean an N-series filter that is at least 95% efficient. Chemical cartridges that include particulate filter elements will carry a similar marking that pertains only to the particulate filter element. New classes of non-powered particulate respirators require new decision logic for selection of the proper respirator. The selection process for using the new particulate classification is outlined as follows: (1) The selection of N-, R-, and P-series filters depends on the presence or absence of oil particles, as follows: If no oil particles are present in the work environment, use a filter of any series (i.e., N-, R-, or P-series). If oil particles (e.g., lubricants, cutting fluids, glycerin, etc.) are present, use an R- or P-series filter. Note that N-series filters cannot be used if oil particles are present. If oil particles are present and the filter is to be used for more than one work shift, use only a P-series filter (e.g. guide: N for Not resistant to oil, R for Resistant to oil; P for oil Proof); and (2) selection of filter efficiency (i.e., 95%, 99%, or 99.97%) depends on how much filter leakage can be accepted. Higher filter efficiency means lower filter leakage.

Other respirator rules or regulations may define that certain classes of filtering-facepieces be used with particular contaminant and/or for certain exposure times based on contaminant concentration levels. So, if sensed workplace conditions regarding particulates indicate contaminant concentration values above or below acceptable limits, such could change the exposure time accordingly. For some products, such as electrical products in the workplace, OSHA requires third-party approval, such as Underwriter Laboratories. Still other OSHA PPE rules and regulations require hard hats, safety glasses, and safety footwear meet specific certification standards. Also, companies using PPE articles typically have the responsibility for ensuring compliance with the appropriate rules, regulations, recommendations, and certifications. Facilities are sometimes allowed to determine their own predetermined criteria based on the particulars of their work environment, PPE article, and the pertinent rules and regulations that govern the former. The present disclosure is not limited to OSHA rules and regulations, but any and all other appropriate rules, regulations, recommendations and guidelines.

In an illustrated exemplary embodiment, the PPE article 120 is an article of respiratory protective equipment (RPE) 120. The RPE article 120 may be coupled to a component 110 used in conjunction with the PPE article. For example, the RPE article 120 may be a 7502 half facepiece respirator that is commercially available from 3M Company of St. Paul, Minn. The component 110 may be a 6001 Series organic vapor cartridge that is commercially available from 3M Company of St. Paul, Minn. The present disclosure is not limited by the foregoing combination of components and PPE articles, but envisions all suitable combinations. Other known types of PPE articles suitable for use in embodiments of the present disclosure include, without limitation, respiratory protection equipment (RPE) protective eyewear, such as visors, goggles, filters or shields, protective headwear, such as hard hats, hoods or helmets, hearing protection, protective shoes, protective gloves, other protective clothing, such as coveralls and aprons, protective articles, such as sensors, safety tools, detectors, global positioning devices, mining cap lamps and any other suitable gear.

In one exemplary embodiment, the information retrieval system 102 includes one or more smart tags 130a-n (collectively, 130); one or more data acquiring devices 140a-n (collectively, 140) that acquire data from the smart tags; and, one or more sensors 145a-n (collectively, 145) that, as will be described, sense for variables that are related to usage of the PPE article being tracked. Given the number of different kinds of smart tags, data acquiring devices, and sensors that can be used, there exists a large number of combinations for the system 102 that can be constructed depending on the PPE articles and the appropriate predetermined criterion. Accordingly, the exemplary information retrieval system 102 is but one of many different and suitable types.

The present disclosure contemplates use of any suitable smart tag known in the art. In one exemplary embodiment, the smart tag 130 is directly attached to the PPE article 120. Essentially, a smart tag is a data carrier that carries data accessible by suitable methods, including, but not limited to, electronic, optical, or other wireless technology. Data on a smart tag may, typically, at least, include tag identification information, such as an identification number (e.g., serial number). In addition, the smart tag 130 may contain other information relating to the article of PPE 120, such as the type of article used; historical information relating to the article, information about the user (who used it, where it was used, under what condition it was used, etc.) maintenance or other type of processing, information about who wrote information onto the smart tag; any requirements relating to the article and its associated component, and/or their use, whether any such requirements have been satisfied, such as any certifications obtained, and any other useful information, such as change-out history, or the working environment. Also, information regarding the user of the article of PPE may be on the smart tag 130; such as, medical information, information relating to fit-testing, training, job responsibilities, seniority or experience, access privileges or any other information.

Smart tags include passive and active types. Generally, passive tags do not include an internal power source and the data carried thereby may be encoded at manufacture. Data information may be acquired from a passive smart tag, for example, radio frequency, microwave, infrared, or other wireless modes; or by optical readers or other appropriate electronic or optical technology. One type of passive smart tag is radio frequency identification (RFID) tag, wherein a transponder carries read-only data. Another type of passive smart tags may be rewritable. RFID technology is known and understood by those skilled in the art and, hence, only a brief description is included herein for facilitating understanding of the present disclosure. Passive RFID type smart tags are typically provided in the form of small labels or the like that include a coiled, etched or stamped antenna, a capacitor, and a substrate on which the components are mounted or embedded. For some metallic smart tags, the metallic portion itself may serve as the antenna. The RFID type smart tag may be embedded in or attached to the PPE articles 120 by any suitable approach. For example, the smart tags may be joinable as by being adhered, fastened, sewn, friction fitted, mechanically clipped, welded (e.g., ultrasonically) or molded, etc. onto or into the components, included as an integral component of the article or securely attached by any suitable means.

Besides passive RFID smart tags, other passive smart tags may include, without limitation, optical kinds including barcode and optical character recognition systems; electromagnetic systems; and acoustomagnetic systems.

On the other hand, active smart tags tend to carry their own internal power source as well as data, and an appropriate antenna for allowing exchanging of their data. The internal power supply may include a micro-battery, a thin film battery, or the like. Active smart tags may be reprogrammable and include, besides an antenna, a microchip to receive and store additional information beyond the information contained in its fixed code. Active smart tags may exchange their data information with data acquiring and/or transmitting devices, such as including, without limitation, readers and/or writers, scanners, and/or data receivers, such as wireless receivers. The exchange may be initiated by the active smart tag itself once it finds a suitable or designated, reader, scanner, or receiver. The active smart tags may transmit their data in response to triggering or interrogating signals, they may actively transmit their data independent of such signals. For instance, the active smart tags may continuously or periodically transmit data to appropriate readers and/or writers, scanners, or receivers. As noted, some active smart tags include the capability to receive and store additional information beyond that contained by its encoded data. Other kinds of active smart tags may be configured to be rewritable. For instance, an active RFID smart tag may be rewritable, as by an RFID reader/writer.

Other kinds of active smart tags include a real time location system (RTLS) smart tag. An RTLS active smart tag is an active tag having a transmitter and a receiver and it communicates with a network according to a particular protocol. RTLS systems can work to determine the position of the smart tag in a 2-dimensional or 3-dimensional space. For example, a RTLS smart tag generally uses one or both of the following wireless location-based methods for determining the position of a smart tag or the object the tag is attached to.

The first is a Time Difference of Arrival (TDOA) method. In one implementation of this method, the smart tag will broadcast a signal to multiple wireless receivers 140 at known locations. The time at which the signal is received by each receiver is measured, and a set of equations can be used to determine the position of the smart tag. Examples of systems using this method are a global positioning system (GPS) or a system using low frequency radio transmitters that use the time interval between radio signals (LORAN). Another example is an active smart tag used in a WiFi system that determines how long a signal takes to reach a receiver. Other companies that use this principle for RTLS systems are AeroScout Inc., Redwood City, Calif.; Nano-Tron Technologies, GmbH, Berlin, Germany; WhereNet, Santa Clara, Calif.; and, Multi Spectral Solutions, Inc., Germantown, Md.

A RTLS may also use a Received Signal Strength Indicator (RSSI) method. This latter method requires tags or fixed transceivers to measure the received power (signal strength) of the incoming signals. Then, using either known variations of signal strength vs. distance from transmitters, or by measuring the signal strengths at various locations and matching these measured strengths to the measured strengths, position can be determined. Companies that provide commercially available products using the RTLS system include Wavetrend, Fairfax Va., and PanGo Networks, Framingham, Mass.

One example of an active smart tag suitable for use in an RTLS system is an Ekahau™ smart tag, which communicates with wireless receivers in a wireless local area network (WLAN) through IEEE 802.11b and 802.11g standards. The Ekahau™ smart tag is commercially available from Ekahau, Inc., Reston Va. and may be used in the present exemplary embodiment. Other examples of suitable smart tags may be provided, and include those, such as described, in U.S. Pat. No. 6,853,303, which is incorporated herein.

As noted, the data from the smart tag may be acquired by data acquiring devices 140, such as readers 140, readers/writers 140, scanners 140, or receivers, such as wireless receivers 140, as well as other suitable devices. A reader or scanner may include an antenna for transmitting a trigger signal to a smart tag and receiving a return signal from the tag containing information. The data acquiring devices 140 may be placed in any one or more of the critical spots of the process including but not limited to the area where the PPE articles 120 are handed out to the individual. In some exemplary embodiments, one or more data acquiring devices 140, such as readers or scanners 140 are hand-held. For example, a receiver 140 may be a wireless node of a wireless local area network (WLAN) that may provide an internet access point.

The readers 140 may be linked to a remote programmable electronic system 150 through the network 160. The programmable electronic system 150 includes functionalities that enable tracking usage of the PPE articles against at least a predetermined criterion. These may include, but are not limited to, certifications regarding servicing, repairing, cleaning, maintaining, decontaminating, or other processing the PPE articles. For example, if the cumulative exposure time of the RPE article, in the workplace exceeds a certification value(s); the concentration level(s) of particular contaminants exceed certification value(s); the presence of unexpected contaminants in the working environment; persons with particular profiles should not be exposed to various contaminants; particular kinds of PPE articles should or should not be used when certain contaminants are present.

Figure 5:
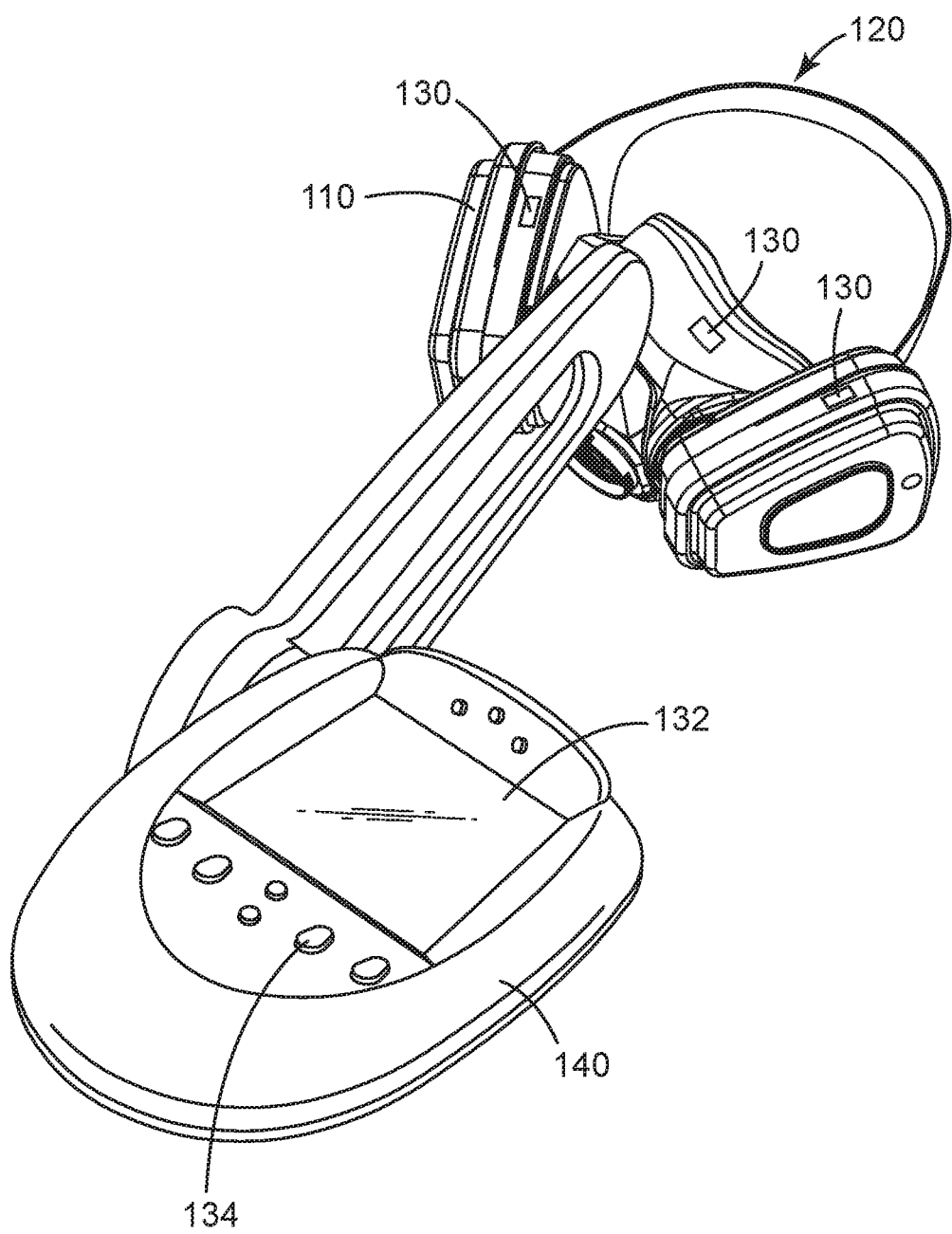
FIG. 5 is a schematic view of a smart tagged RPE including a portable reader.

As illustrated in FIG. 1, the reader 140a may be stationed at the entrance of the work environment 125 and acquires relevant data of the wearer; component 110, and the PPE article 120, such as one or both of: at the start of the workday or shift and at the end of the work day or shift. The readers may be in a variety of one or more other locations, such as where the components are removably coupled to the PPE article. This information is sent to a database of the computer system 150 for the purposes which will be described. Alternatively or additionally, one or more readers 140 may be located within the actual work environment 125 so as to provide opportunities for wearers obtaining readings in the work environment 125. Alternatively or additionally, a portable reader 140 may be utilized (see FIG. 5), such as where the PPE articles 120 are issued prior to entering the work environment. A typical portable reader 140 may have a display 132 and keypad 134 for data input and are wirelessly connected to the network 160. The portable reader 140 may be used when the tagged PPE articles are in the work environment 125 or at the end of a work shift. The present disclosure does not place limitations on the locations or timing of reading of the tagged PPE articles.

Exemplary suitable sensors 145 of some exemplary embodiment may include, without limitation, measurement of the following analytes/parameters: electromagnetic radiation (such as thermal and visible), ionizing radiation, nuclear radiation, chemicals (such as liquids, solids, vapors, gases and mists/aerosols), biological analytes, particulates, noise, heat stress, motion, as well as others. The transducers may be of the electrical or optoelectronic type. The sensors 145 may be mobile or stationary in the work environment and connected, as for example, by wireless to the network. In the mobile mode, the sensors 145 may be disposed on the PPE or on the component. The sensed information data is generally related to the usage of the PPE article being tracked as will be explained. The data, as noted, includes, without limitation, concentration levels, types of contaminants, presence or absence of contaminants, insufficient or no current to run a circuit of the PPE article, inadequate pressure for a self-contained breathing apparatus (SCBA), insufficient or no battery power, breakthrough of a chemical through a filter, or inoperable safety mechanisms. The present disclosure is not limited by these examples since what is sensed encompasses any known factors that may relate in any way to the condition or use of the PPE articles.

Figure 3:
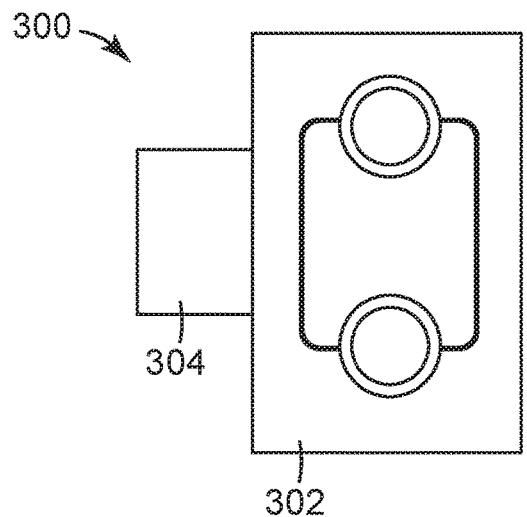
FIG. 3 is a schematic view of a smart tag coupled to a sensor.
Figure 4:
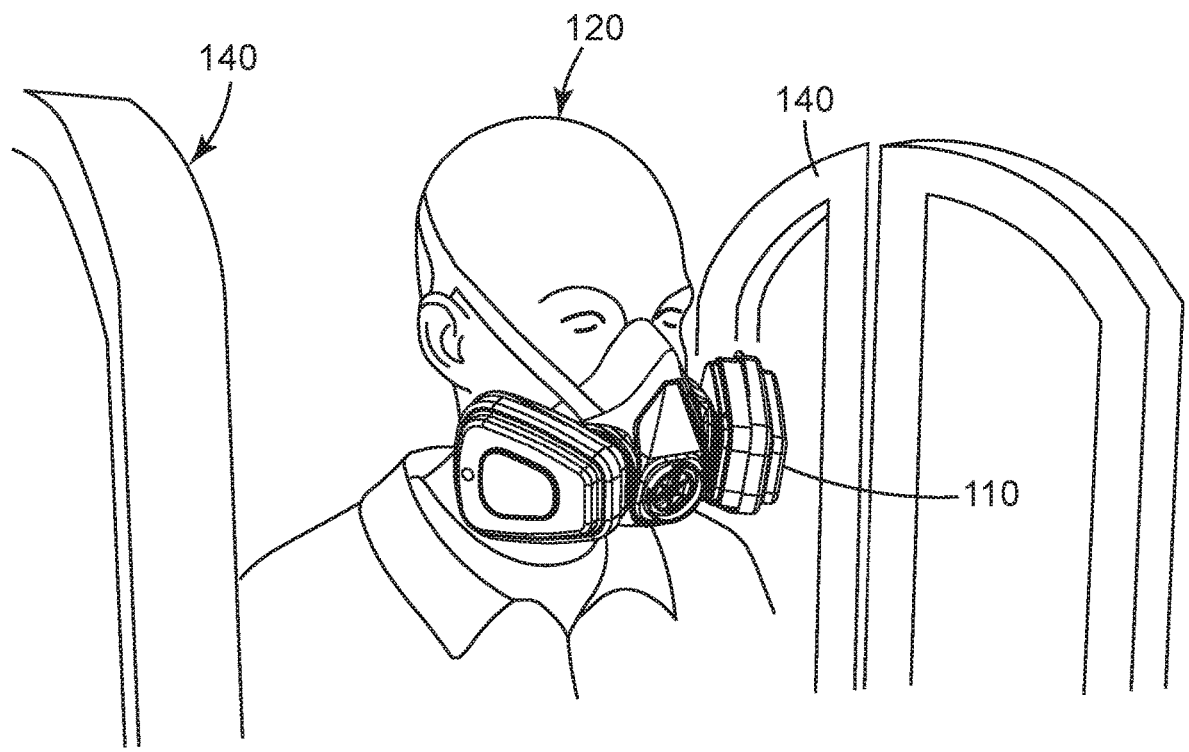
FIG. 4 is a schematic view of a wearer passing an exemplary data acquisition portal which may be used in some exemplary embodiments utilized in the system of FIG. 1 and wearing a smart tagged RPE article.

Reference is made to FIG. 3 for illustrating a combination sensing and smart device 300 that may be attached directly to an article of PPE (not shown). The sensing and smart device 300 includes a combination of photo-ionization detector (PID) sensing device 304, and the Ekahau™ smart tag 302. The functionalities of the sensing device and the smart tag remain the same despite being physically coupled together. The combination sensing device 300 may also provide location information that may be mapped to identify a location(s) in which the concentration levels may change (e.g., spike).

The network 160 may include, without limitation, a local-area network (LAN), wide area network (WAN), the internet, or a wireless network, such as a wireless local area network (WLAN). The programmable electronic system 150 may represent any type of computer system, programmable logic devices, or the like. The computer system 150 may include server computers, client computers, PC-based servers, minicomputers, midrange computers, mainframe computers; or other suitable devices. In some exemplary embodiments, the computer system 150 may include portable computer systems including laptops, handheld computer systems. In addition, the system 100 may include one or more local computer systems 170 located in the work environment 125. As such, workers may be able to obtain pertinent data, for example, a real-time assessment of the condition of the PPE article while in the work environment 125. The local computer system 170 typically includes portable computer systems including laptops, handheld computer systems. The local computer system 170 may also include other computer systems, such as, client computers, PC-based servers, minicomputers, midrange computers, mainframe computers; or other suitable devices.

Figure 2:
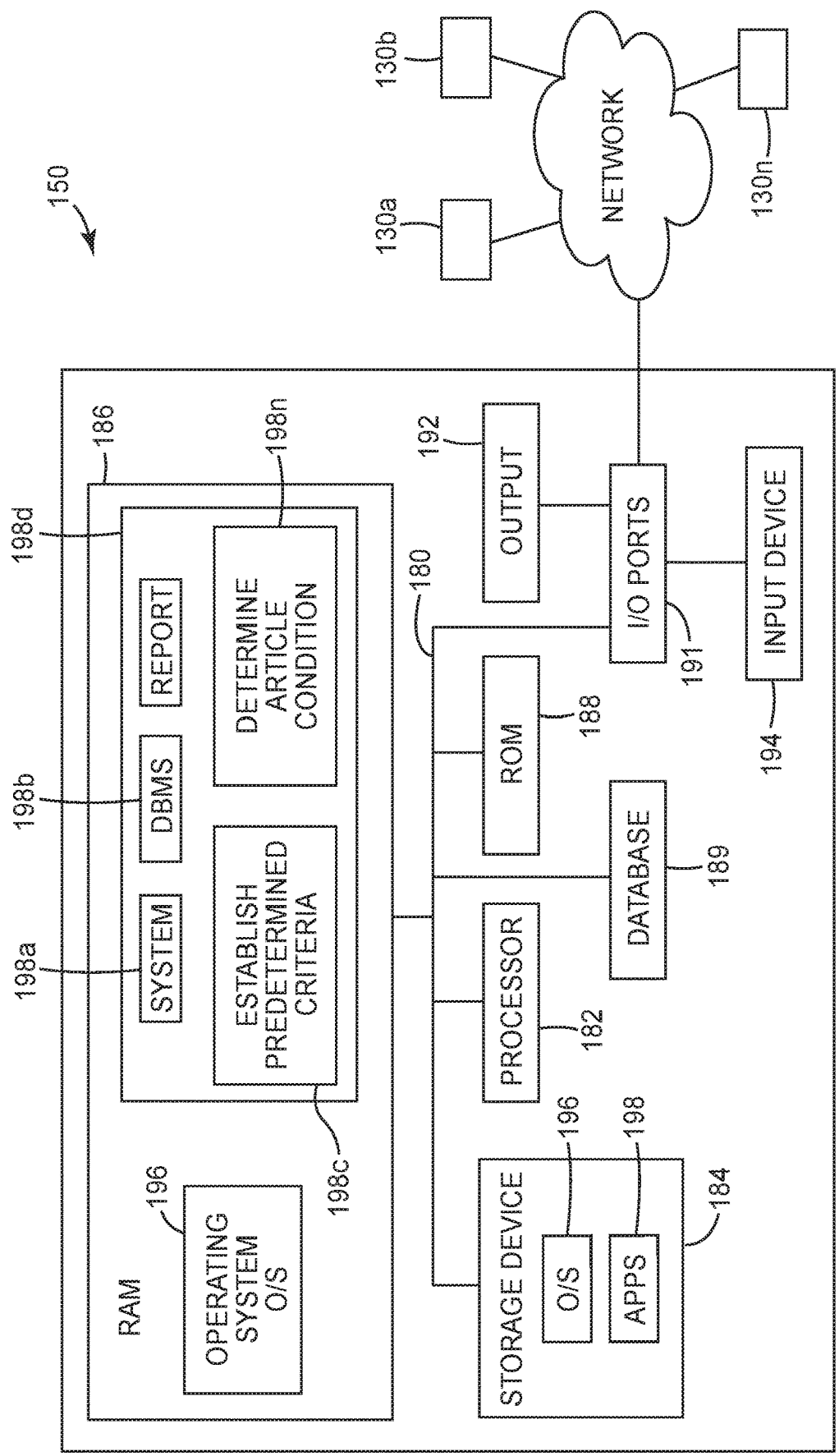
FIG. 2 is block diagram of a computer system utilizable in an information retrieval system of the present disclosure.

With continued reference to FIG. 2, there is depicted a server computer system 150. It is depicted as comprising at least one system interconnect bus 180 to which various components are coupled and communicate with each other. Coupled to the system interconnect bus 180 is at least a single processor unit 182, storage device 184, memory such as random access memory (RAM) 186, read only memory (ROM) 188, a relational database management system (DBMS) 189, and input/output (I/O) ports 191. The relational database is a computer database management system 189 controlling the storing, updating, and retrieving of data to database files for use in tracking usage of PPE articles against the one or more predetermined criteria under the control of the applications to be described hereinafter. The database files contain all relevant information pertaining to the operational parameters of the readers. Furthermore, one or more output devices 192 such as a display, as well as one or more user interface input devices 194, such as a keyboard and/or pointing device is respectively coupled to the I/O ports 191. In known fashion, the output and input devices 192 and 194; respectively permit wearer interaction with the computer system 150. The I/O port 191 typically includes various controllers (not shown) for each input device 194, such as a keyboard, mouse, joystick, and the like, as well as the output device 192, such as an Ethernet network adapter, infrared device and display (not shown). The processor 182 controls the input device 194 which provides a user interface for allowing a wearer to access information, such as usage history of PPE articles being tracked.

The processor unit 182 may be any suitable processor and sends and receives instructions and data to and from each of the computer system's components that are coupled to the system interconnect bus 180 to perform system operations based upon the requirements of the computer system's operating system (OS) 196, and other specialized application programs 198a-198n (collectively 198).

The ROM 188 typically controls basic hardware operations. The storage device 184 may be a permanent storage medium, such as a hard disk, CD-ROM, tape, or the like, which stores the operating system 196 and the specialized applications programs 198. The RAM 186 is volatile memory. The contents of the RAM 186 may be retrieved from the storage device 184 as required. Illustratively, the RAM 186 is shown with the operating system 196 and application programs 198 concurrently stored therein. The program code of the operating system 196 and/or application programs 198 is sent to the RAM 186 for temporary storage and subsequent execution by the processor 182. Additionally, the RAM 186 is capable of storing files from the operating system 196, as well as files from one or more application programs.

An information retrieval system application program(s) 198a is one typically utilized for controlling operations of the information retrieval system 102 including the functionalities described herein with respect to the smart tags 130, data acquiring devices 140, and sensors 145. Provision is made for a suitable database management system application 198b to run the database 189 in a manner consistent with the present disclosure. Also, provision is made for an establish predetermined criteria application 198c. This may, in some cases, be a software application provided by a manufacturer of the PPE article that are to be tracked. In some exemplary embodiments, this software application may be used to establish conditions for proper usage of the PPE article as determined by the rules and regulations established by the government, insurance company or other entity interested in the results. The establish condition determining application 198c is updatable to establish a new or current criteria related to actual conditions of the PPE article in the working environment, as for example, by using the data acquired.

A report generating application 198d is provided that may generate reports containing a variety of data in different reporting formats tailored for purposes including those described below. These reports may be generated to allow workers, supervisors, health professionals to access the history and status of articles; their medical information, information relating to fit-testing, training, job responsibilities, seniority or experience, access privileges or any other information, history of PPE article servicing, maintenance, change-out, as well as other information.

The determining PPE condition application 198n of the present disclosure enables determining the conditions of the tagged PPE articles 120 following retrieval of smart tag information and sensed data information against at least one predetermined criterion established by the establish predetermined criteria application 198c.

Figure 6:
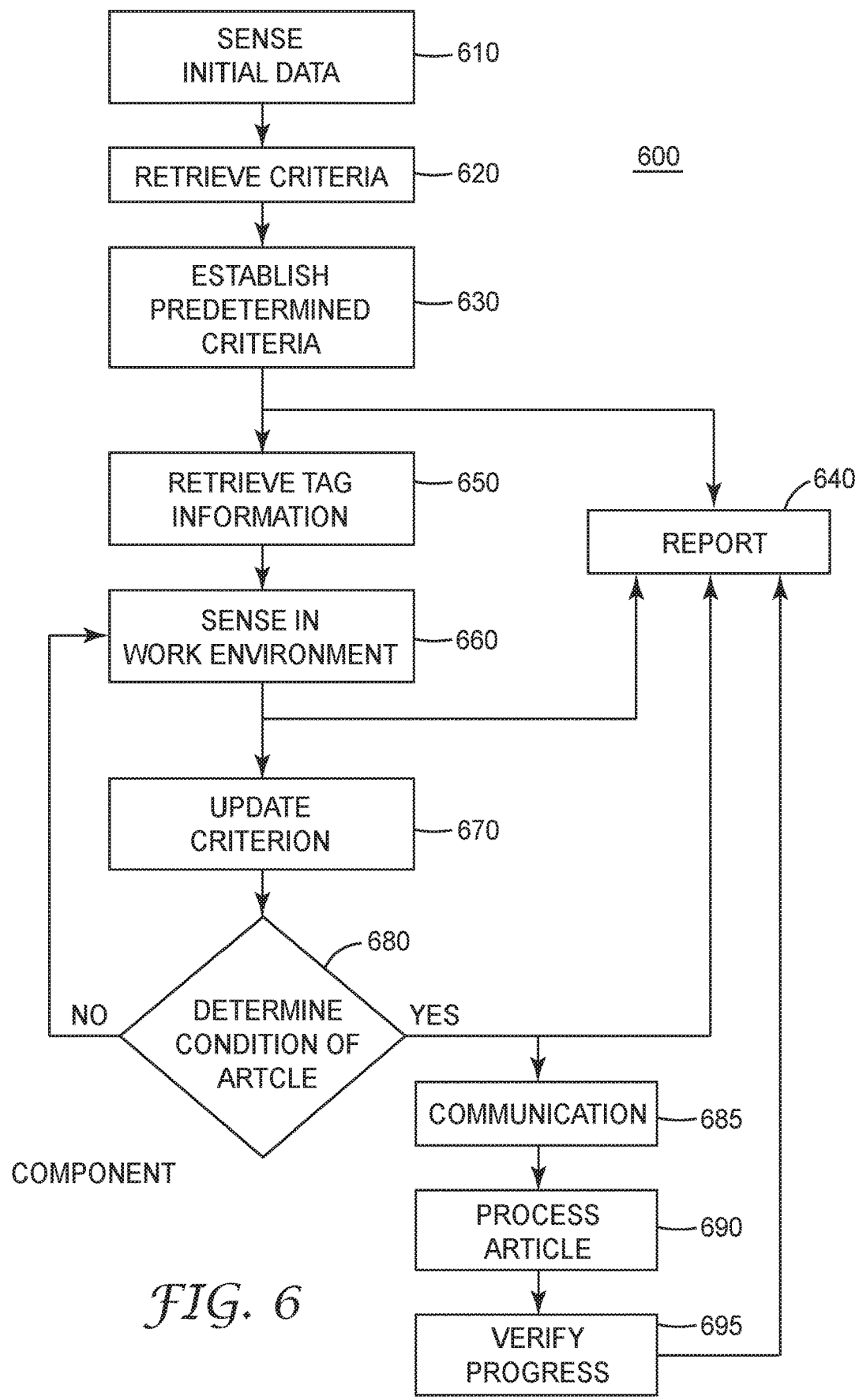
FIG. 6 is a flow diagram of one exemplary embodiment of a process that may be performed according to the present disclosure.

Reference is made to FIG. 6 for illustrating one exemplary embodiment of a PPE article condition determining process 600 that may be implemented by the PPE article condition determining system 100. The PPE article condition determining process 600 enables determining the condition of the PPE articles 120 tagged with a smart tag 130 after processing data received by the smart tag and/or one of the sensors. The term "condition" as utilized in the present application means the particular state of one or more factors that affect the operational life or usefulness of one or more PPE articles. In this exemplary embodiment, the condition being determined is if the RPE 120 should be serviced after exposure to contaminants for a certain exposure over time.

In a Sense Initial Condition block 610 of the PPE article condition determining process 600, sensing is performed by one or more of the sensors 145. In this embodiment, the type of PPE articles 120 being tracked determines which variables in the working environment should be sensed and, therefore, which sensors to be used. Since conditions of respirators are being determined in this exemplary embodiment, the sensor 145 is of the type that collects data bearing upon the PPE article's condition relative to its servicing. In particular, concentration levels of a particular hazardous material over a period of time may be sensed as by the PID sensor 145. As will be explained, the concentration levels may assist in establishing a predetermined criterion regarding the servicing condition of the tagged PPE article. The initial sensed data from the sensor 145 that is collected may reflect low, average, and peak concentration levels of the particular hazardous material(s). Other sensors may detect for the presence of other contaminants that, for example, may be incompatible with the respirator being used. While hazardous materials are being monitored in the exemplary embodiment, the present disclosure envisions that there are no limits on the variables that may be sensed and the relationship these variables have in determining the condition of the PPE article. For example, variable factors relating to other aspects of usage of the RPE article may include: charge of a battery, amps in a circuit, and circulating air pressure of their respirator. The condition determining process allows this data to be forwarded to the database.

The PPE article condition determining process 600 then proceeds to Retrieve Criteria block 620, whereat the establish a predetermined criteria application 198c retrieves at least one appropriate predetermined criterion (or criteria) for the PPE article whose condition is being determined. If the PPE article being monitored is a respirator, the pertinent criterion that is relevant to its condition (e.g., servicing) may be selected. The set of criteria is stored in memory. The set of criteria may be obtained from many different sources that provide guidance on the proper servicing of the PPE article as noted above. The set of criteria may be downloaded, for example, from the internet. Typically, the manufacturer of the PPE article may provide the set of criteria that is relevant to the condition of the PPE article. The set of criteria may be developed by government, industry, the company operating the system 100, an insurance company, standards' bodies, and persons of interest, such as a safety officer, industrial hygienist, or the like. In the present exemplary embodiment, the set of criteria may relate to minimum or maximum exposure times that a respirator may safely operate before being serviced. Another example of a set of criteria relates to proper battery charge of an PPE article relative to acceptable limits of performance of the PPE article. Still another example of a set of criteria that governs use of when a respirator should be serviced, repaired, or otherwise treated, is based on inadequate pressure existing, such as in a self-contained breathing apparatus (SCBA).

Following the Retrieve Criteria block 620, the condition determining 600 proceeds to an Establish Predetermined Criteria block 630. In the block 630, the initial data that may be sensed in the block 610 is processed in the database by the establish predetermined criterion application 198c. As a result, there is established a predetermined criterion for the PPE article 120 in the actual working environment. In such an exemplary embodiment, the predetermined criteria application(s) 198c analyzes the collected monitored data in terms of the set of criteria retrieved in the block 620 to determine the predetermined criterion that will determine if the condition of the PPE article, during its actual use in the working environment, is satisfied. For example, based on the initial concentration levels in the work environment, a maximum exposure time for the respirator is then determined before it should be serviced. The predetermined criterion takes into account the exposure time recommended or required for the respirator in the work environment.

The condition determining process 600 may further include a Reporting block 640 that follows the Establish Predetermined Criteria block 630 under the control of the reporting application 198b. The Reporting block 640 is capable for generating a report relevant to a wide variety of subjects including, but not limited to, the condition of the PPE article, the worker, or even its associated one or more components, the initial sensed data, the work environment, and other pertinent information. Typically, the Reporting block 640 generates a report in a format acceptable by an entity requesting the report, for example, the business entity using the system 100, or a governmental agency, such as OSHA. While the Report block 640 follows Establish Predetermined Criteria block 630, reports may be generated at any one or more points in the process. The reports may be generated by the workers or other persons of interest or even in response to requests by the government. The reports generated may be transmitted across the internet as well. There is no time limit to generating the reports.

The PPE article condition determining process 600 proceeds to a Retrieve Tag Information block 650. In this embodiment, the system 102 retrieves or acquires the data, as noted above, from the smart tags 130 by the data acquiring devices 140, such as a receiver 140, as well as the sensors 145. The smart tag 130 of this embodiment may be an Ekahau™ type 130 to provide location information as well as the data of the smart tag. Other smart tags can be provided. The receiver 140 may be located in any number of places, such as the entrance to a work environment 125. In particular, retrieving information from the smart tag 130 may provide data as to when and where the wearer enters the working environment, exits the working environment, or passes another location. Optionally, in order to identify the wearer, the latter may present his/her badge to an appropriate data acquiring device 140. The smart tag 130 or the badge may also include other data regarding the wearer, such as medical, fit test, job description, seniority, training, and other qualifications. The retrieved data is forwarded to the database 189 of the computer system 150, and, if operational, the local computer system 170. The data may include the identification of an article, date, and/or timestamp, as well as the location of the data acquiring device. The present disclosure envisions that the retrieving tag information may occur more than once and at any suitable number of points in the determining process.

The PPE article condition determining process 600 then proceeds to the Sense In Work Environment block 660. In the Sense In Work Environment block 660, the sensor 145, such as the PID sensor 145, is operable for providing current sensed data regarding, for example, current concentration levels of benzene vapor in the work environment 125. This data is forwarded to the database. The PPE article condition determining process 600 may proceed to the Update Criterion block 670. In the Update Criterion block 670, the data from the database from the sensor 145 is acted upon by the establish predetermined criteria application 198c, where a new analysis is conducted to determine whether an update predetermined criterion is to be used. Such updating enhances the overall advantages provided by the present disclosure. While the Sense In Work Environment block 660 and the Update Criterion block 670 are illustrated, they need not be present in the PPE article condition determining process 600. In such a case, the process 600 may proceed to the Determine Condition of PPE Article block 680.

In either event, the PPE article condition determining process 600 then may proceed to the Determine Condition of PPE Article block 680. In the Determine Condition of PPE Article block 680, the condition determining application 198n determines if the condition of the PPE article satisfies the initial or updated criterion. In particular, in an exemplary embodiment, the exemplary determination is made as to whether a respirator has an exposure time that exceeds the recommended exposure time of the article in the working environment as determined in the Establish Predetermined Criterion block 630. If the actual exposure time does exceed the recommended exposure time then the respirator has satisfied the predetermined criterion, that the article should be serviced. In the Determine Condition of PPE Article block 680, the article has satisfied the predetermined criterion servicing (i.e., Yes) since its actual exposure time does exceed the recommended exposure time, when compared to the recommended exposure time, indicated in the Establish Predetermined Criteria block 630 or the Updated Criterion block 670. Conversely, the servicing condition is not satisfied (i.e., No) if the actual exposure time does not exceed recommended exposure time as determined in the Establish Predetermined Criteria block 630 or the Updated Criterion block 670.

The PPE article condition determining process 600 includes a Communicate block 685, whereat compliance or non-compliance is communicated, using any known communication methodology, to appropriate persons, or reporting entities. Such a communication may be transmitted to the user, the database, the user's supervisor, industrial hygienist or other appropriate personnel. The process of this block may be occurring at other times. In one exemplary embodiment, such communications may be made as a message to display screen of the computer or to a personal digital assistant (PDA). It will be appreciated other suitable software applications may be used to provide such communication. In one exemplary embodiment, such determinations may be made as a message to display screen of the computer or to a personal digital assistant (PDA). It will be appreciated other suitable software applications may be used to provide such communication. In some exemplary embodiments, such communications may include an alarm or audible signal to appropriate persons including the user and/or supervisor.

The PPE article condition determining process 600 also includes a Process Article block 690 that may follow the Communicate block 685. A wide variety of processes may be performed to handle the article, such as cleaning, refurbishing, disposal or the like. A wide variety of disposal methods are contemplated, for example, being displaced in a bin, this will ensure that the PPE article will not be used until some other steps are undertaken.

The PPE Article Condition Determining process 600 may then proceed to Verify Processing block 695. In the Verify Processing block 695, a data acquiring device p may be stationed adjacent to the processing area, such as a disposal bin, for acquiring relevant identification data from its smart tag 136 that the PPE article 120 has been processed. The verification data is transferred to the server's database for storage in the internal memory and subsequent use. As a consequence, processing is duly recorded in the database.

EXAMPLES

The following are prophetic examples using the improved process and system of the present disclosure.

Example 1

A photoionization detector (PID) sensor 145, for example, an EntryRAE PID from RAE Systems, San Jose, Calif., may be used to monitor levels of volatile organic compounds at a fiberglass coating facility. Based on compositional knowledge of the fiberglass composite material being used onsite, it is known that styrene is a primary hazardous vapor present within the facility. Initial data may be taken from a log (20 minute) of styrene concentrations obtained with the PID prior to actual use of the respirator. In the working environment, spikes in concentration levels may occur, such as spikes above 200 ppm, at different time intervals, (e.g., 9 minute and 13 minute). A NIOSH-defined occupational exposure limit (OEL) (predetermined criteria) for styrene is 20 ppm. At 200 ppm and above (i.e., 10× the OEL) the styrene concentration is above the protection factor for a half-face piece air purifying respirator. The data from the PID may be sent to the database 189 of the computer system 150. These readings are processed by the condition determining mechanism for determining if the above condition satisfies the predetermined criteria to determine the condition of the PPE article in terms of its servicing or replacement.

Example 2

Initial real time styrene concentration data, are collected using a wireless PID worn on a worker, such as obtained by the PID sensor 145. This data is documented within the database. Based on the cumulative concentration data gathered over a multi-day period, it is determined that the respirator used by the worker should be disposed of after 24 hr. of use. Such a determination was based on NIOSH regulations governing use of the respirator in a workplace having the collected expected styrene concentrations that are assumed to exist, when the respirator is actually used. Both the worker and the safety person may be notified of the appropriate servicing or change-out schedule. Actual use of the respirator is monitored by the smart tag 130 and the sensor 145. By continuing to monitor exposure data over time, the condition determining process can determine whether the respirator is complying with the NIOSH regulations. Accordingly, the worker and the safety person may take appropriate measures based on the determination. For example, changes in workflow or in engineering controls could make a more stringent or if necessary change the schedules of use.

Example 3

Real-time styrene concentration data are collected using a wireless PID on worker within a fiberglass coating facility, with the data documented within a central database. In this example, the PID 145 is also coupled with an Ekahau™ RTLS smart tag 130, which provides location information of the wearer within the working environment using a wireless network. The concentration and location data are sent to a central database where they are linked via their time stamp data. By monitoring the data and locations over a period of weeks, a determination may be made that a worker is exposed to the highest periodic concentration of styrene within a particular coating bay within the working environment. With such information, efforts may be undertaken by appropriate personnel to correct the matter, such as providing additional ventilation at the vicinity of the bay. Additionally, the appropriate personnel are able to make sure that the appropriate PPE with sufficient protection factor is worn only within specific areas of the working environment.

Example 4

The sensors of Examples 1, 2, or 3 are utilized via incorporation on or inside the personal protection equipment of a worker to monitor the actual internal environment surrounding the worker. This data is sent wirelessly to the central database to produce reports (e.g., graphics or tables) indicating the cumulative exposure and protection provided for the worker during certain time periods.

It will be appreciated that numerous and varied other arrangements may be readily devised in accordance with these principles by those skilled in the art without departing from the spirit and scope of the invention as claimed.

It will be appreciated that based on the above description, aspects of the disclosure include methods and systems for determining conditions of articles, such as PPE articles, by determining if they satisfy at least one criterion. Further aspects of the disclosure include methods and systems for determining conditions of articles, as noted above, by updating such predetermined criteria to reflect existing conditions in the working environments. Further aspects of the disclosure include methods and systems utilized for ensuring worker safety, and preventing needless discarding of articles by keeping the predetermined criteria contemporaneously valid. Still further aspects of the disclosure include methods and systems utilized for achieving the foregoing economically and expeditiously. Still further aspects of the disclosure include methods and systems utilized for locating working environments in which monitored concentration levels reach hazardous or potentially hazardous levels.

Although the methods and systems of the present disclosure have been described with reference to specific exemplary embodiments, those of ordinary skill in the art will readily appreciate that changes and modifications may be made thereto without departing from the spirit and scope of the present disclosure.

What is claimed is:

1. A system comprising:
a personal protection article configured with a smart tag;
a computing device comprising one or more computer processors, and a memory comprising instructions that when executed by the one or more computer processors cause the one or more computer processors to:
configure at least one predetermined criterion that corresponds to the personal protection article in a working environment, wherein the working environment is external to the personal protection article;
receive sensed data, generated by at least one sensing device that is related to a hazard level for a hazard the working environment, a hazard type for the hazard in the working environment, a presence of the hazard in the working environment, or an absence of the hazard in the working environment;
receive smart tag data using the smart tag associated with the personal protection article, the smart tag data including an identification of the personal protection article;
store the sensed data sensed by the at least one sensing device and the smart tag data that is from the smart tag, and a timestamp indicative of when the smart tag data was received;
process the sensed data and at least part of the smart tag data to determine a condition that corresponds to operation of the personal protection article in the working environment; and
perform, based at least in part on the at least one predetermined criterion pertaining to the personal protection article, at least one operation in response to the determination of the condition that corresponds to the operation of the personal protection article in the working environment.

2. The system of claim 1, wherein the respective smart tag is physically attached to the personal protection article.

3. The system of claim 1, wherein to perform the at least one operation the memory comprises instructions that when executed cause the one or more computer processors to generate at least one report relating to the condition of the personal protection article.

4. The system of claim 1, wherein to perform the at least one operation the memory comprises instructions that when executed cause the one or more computer processors to generate at least one report relating to at least one of the sensed data or the smart tag data.

5. The system of claim 1, wherein to determine a condition of the personal protection article the memory comprises instructions that when executed cause the one or more computer processors to determine the particular condition based on a condition determining mechanism in a data processing system.

6. The system of claim 1, wherein to perform the at least one operation the memory comprises instructions that when executed cause the one or more computer processors to communicate information that is based at least in part on a determination whether a real-time assessment of the condition of the particular personal protection article satisfies the at least one predetermined criterion pertaining to the personal protection article.

7. The system of claim 1, wherein to perform the at least one operation the memory comprises instructions that when executed cause the one or more computer processors to generate at least one output.

8. The system of claim 7, wherein the at least one output is a visual or audible output.

9. The system of claim 8, wherein the condition comprises at least one of a concentration level, a type of contaminant, a presence or absence of contaminant, inadequate pressure for a breathing apparatus, battery power, breakthrough of a contaminant through a filter, a reading from the personal protection article, or an inoperable safety mechanism.

10. The system of claim 9, wherein the condition comprises a first concentration level of a contaminant detected in a work environment, the at least one predetermined criterion comprises a second concentration level, and the first concentration level is greater than the second concentration level.

11. The system of claim 9, wherein the condition comprises a first type of contaminant detected in a work environment, the at least one predetermined criterion comprises a second type of contaminant, and the first type of contaminant is the same as the second type of contaminant.

12. The system of claim 1, wherein to perform the at least one operation, the memory comprises instructions that when executed cause the one or more computer processors to send at least one of the sensed data or the smart tag data to another computing device.

13. The system of claim 1, wherein the smart-tag comprises at least one of a WiFi device or an RFID device.

14. The system of claim 1, wherein to perform the at least one operation the memory comprises instructions that when executed cause the one or more computer processors to output a location that corresponds to a concentration level that satisfies the at least one predetermined criterion.

15. The system of claim 1, wherein the personal protection article comprises at least one of respiratory protection equipment, protective eyewear, protective headwear, hearing protection, protective shoes, protective gloves, protective clothing, a tool, a detector of an air contaminant, a global positioning device, or a mining cap lamp.

16. The system of claim 1, wherein the sensed data is based at least in part on at least one of electromagnetic radiation, ionizing radiation, nuclear radiation, a chemical, a biological analyte, a particulate, noise, heat stress, motion, or usage or operation of the personal protection article.

17. The system of claim 1, wherein the predetermined criterion is an exposure limit, wherein the condition is an exposure to a hazard, wherein to perform the at least one operation the memory comprises instructions that when executed cause the one or more computer processors to generate a visual or audible output in response to the exposure to the hazard satisfying the exposure limit.

18. The system of claim 1, wherein the computing device comprises a display and the computing device is configured to communicate using the Internet.

19. A personal protection article comprising:
at least one microchip;
an antenna;
a sensing device configured to sense data that is based on a working environment;
a power supply;
a housing comprising the at least one microchip, the sensing device, and the power supply;
wherein the at least one microchip is configured to:
send, via wireless communication to a computing device, smart tag data that includes an identification of the particular personal protection article;
send, via wireless communication to the computing device, sensed data from the sensing device that causes the computing device to (i) process the sensed data and at least part of the smart tag data to determine a condition that corresponds to operation of the personal protection article in the working environment and (ii) perform, based at least in part on at least one predetermined criterion pertaining to the personal protection article, at least one operation in response to the determination of the condition that corresponds to the operation of the personal protection article in the working environment, wherein the sensed data is related to a hazard level for a hazard the working environment, a hazard type for the hazard in the working environment, a presence of the hazard in the working environment, or an absence of the hazard in the working environment, wherein the at least one predetermined criterion configured at the computing device corresponds to the personal protection article in the working environment, wherein the working environment is external to the personal protection article; and
store at least part of the smart tag data and, and a timestamp indicative of when the smart tag data was received.

20. The personal protection article of claim 19, wherein in response to sending at least one of the sensed data or the smart tag data to the computing device, the at least one microchip is configured to receive data that is processable by the personal protection article.

* * * * *